United States Patent [19]

Zobele et al.

[11] Patent Number: 5,095,647
[45] Date of Patent: Mar. 17, 1992

[54] APPARATUS TO KEEP FLYING INSECTS, PARTICULARLY MOSQUITOES, AWAY FROM PEOPLE

[75] Inventors: Franco Zobele; Giovanna Z. Lipparini, both of Trento, Italy

[73] Assignee: Zobele Industrie Chimiche S.p.A., Trento, Italy

[21] Appl. No.: 591,705

[22] Filed: Oct. 1, 1990

[30] Foreign Application Priority Data

Sep. 29, 1989 [IT] Italy .................. 21878 A/89

[51] Int. Cl.$^5$ .................................... A01M 19/00
[52] U.S. Cl. .................................... 43/125; 43/129; 239/59; 239/135; 239/136
[58] Field of Search .............. 43/107, 125, 129, 1; 239/44, 49, 50, 53, 55, 56, 58, 59, 135, 136; 223/181, 187

[56] References Cited

U.S. PATENT DOCUMENTS

| | | | |
|---|---|---|---|
| 2,176,345 | 10/1939 | Hurwitt | 43/131 |
| 2,681,252 | 6/1954 | Tuttle | 222/187 |
| 3,431,393 | 3/1969 | Katsuda | 219/274 |
| 4,467,177 | 8/1984 | Zobele | 43/129 |
| 4,621,768 | 11/1986 | Lhoste et al. | 239/59 |
| 4,663,315 | 5/1987 | Hasegawa et al. | 239/44 |
| 4,745,705 | 5/1988 | Yamamoto et al. | 43/125 |
| 4,768,676 | 9/1988 | Kaneko | 239/44 |

FOREIGN PATENT DOCUMENTS 0362397 4/1990 European Pat. Off. .
2095116 9/1982 United Kingdom .
2194442 3/1988 United Kingdom .

Primary Examiner—Richard K. Seidel
Assistant Examiner—Chuck Y. Mah
Attorney, Agent, or Firm—Young & Thompson

[57] ABSTRACT

In order to keep flying insects, especially mosquitoes, away from people, an apparatus has been developed. The apparatus includes a box (A, A") enclosing a heat source (10, 50), provided with at least one vertically oriented flat wall (13', 53'), and a container (C, C') holding an evaporable liquid chemical product. A wick (14, 54), wrapped in an impermeable coating or sheath (19, 59), has a rectangular cross-section and penetrates inside the container (C, C'). A free portion (14", 54") of the wick (14, 54) is devoid of the coating or sheath (19, 59) and extends upwards from the container (C, C') with its largest side (14''', 54''') being disposed parallel to but spaced from the heat source (10, 50). Inside the container (C, C'), the entire length (L) of the wick (14, 54) is surrounded by the coating or sheath (19, 59), except for the extreme lower free portion (14', 54') into which the liquid is absorbed and rises exclusively by capillarity to the far upper free portion (14", 54"), where the wick (14, 54) is heated by the heat source (10, 50) so that the liquid evaporates and passes into atmosphere.

14 Claims, 3 Drawing Sheets

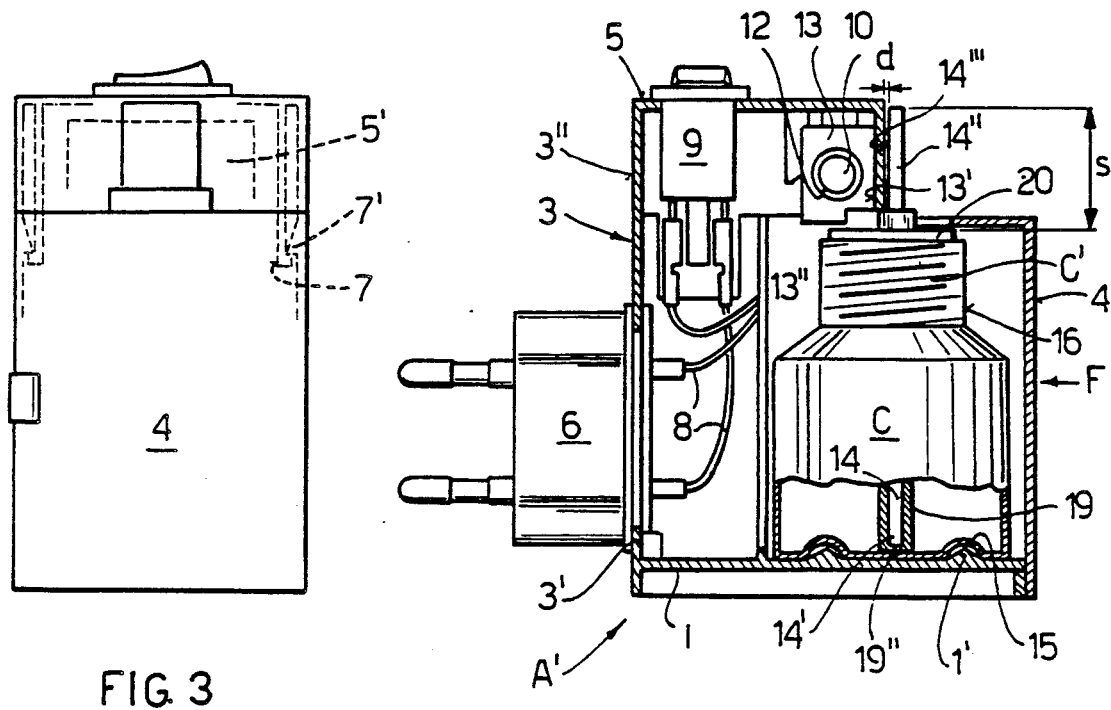
FIG. 1
FIG. 3
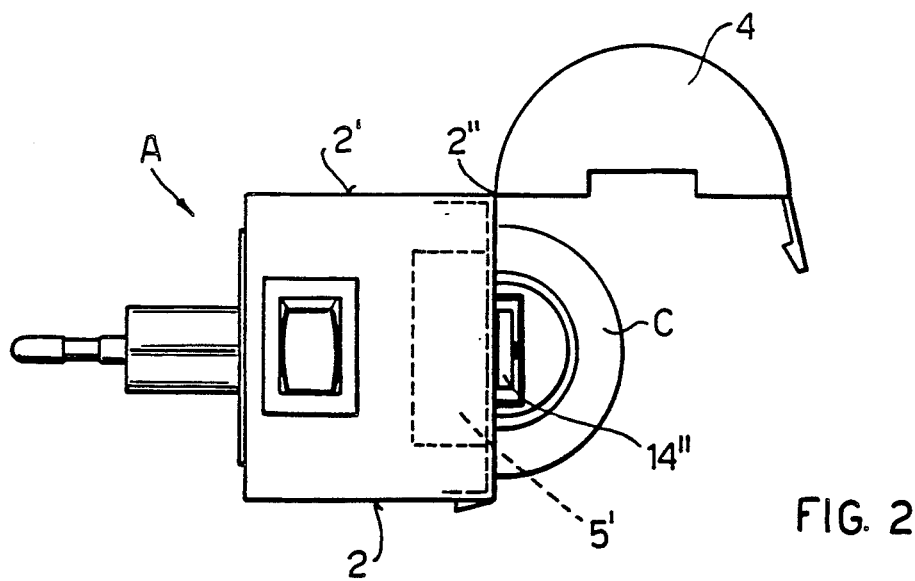
FIG. 2

APPARATUS TO KEEP FLYING INSECTS, PARTICULARLY MOSQUITOES, AWAY FROM PEOPLE

BACKGROUND OF THE INVENTION

1. Field of the Invention

The present invention concerns an apparatus for keeping flying insects, especially the extremely annoying mosquitoes, away from people.

In particular, the apparatus comprises a box enclosing a tank containing a liquid chemical product which is soaked up by a wick after heating an upper portion thereof by means of a heating device.

2. Description of Related Art

There are numerous known apparatuses as marketed everywhere which are designed to protect people from mosquitoes and from other small troublesome insects. These known apparatuses use emanators provided with tablets which, when placed near or adjacent to a heat source, give off the evaporable substances with which they are impregnated. in the form of smoke.

Also known are apparatuses for evaportion by heating a wick in which a liquid chemical product contained in a bottle in drawn up by capillarity into the wick, which is immersed in this product.

A drawback of these known apparatuses in that they generally have a limited capacity for drawing up and evaporating liquid through the wick; moreover, the heat-vaporizing part of the apparatus cannot be placed economically when necessary. Furthermore, in these apparatuses, the bottle containing the liquid chemical product is inserted from below, an operation which proves rather difficult and can easily result in damage to the wick.

SUMMARY OF THE INVENTION

The aim of the present invention is to provide an apparatus which offers long-lasting evaporation of insecticide, air freshener or deodorant, which is capable of evaporating the amount of liquid chemical substance in an efficient, uniform manner and which allows rapid, safe replacement of the container of the liquid substance.

It is characterized in that the box encloses a heat source provided with at least one flat wall set at right angles to the base of a container, located below, which holds the evaporable liquid inside. The liquid penetrates a wick coated with an impermeable material which covers it for virtually the whole of its length, leaving free only the extreme lower portion of the wick and the extreme upper portion which protrudes from the container. The latter portion is disposed near the flat wall of the heat source.

According to a preferred embodiment, the wick has a rectangular cross section, in particular wide and flat, offering a flat surface to the heat source.

The coating-free surface of the extreme lower portion of the wick is very small compared with that of the wick coating itself, whereas the coating-free surface of the extreme upper portion of the wick is greater and has an elongated shape.

Preferably, during operation of the apparatus, the chemical substance in the container is drawn into the wick by capillarity, starting from an area of the wick near the base of the container, where the temperature is lower, until it reaches an area adjacent to a heat source at a distance from said base and outside said container, where the temperature is higher.

Singularly, provison is made for the wick to consist of an absorbent material, in particular cardboard, or in any case a cellulose and/or cotton linter based material, containing about 20% mineral dust, preferably basalt.

An advantageous characteristic according to the invention lies in the fact that the coating of the upper area of the wick is surrounded by a closing device for the container, in the form of an externally cylindrical stopper, which can be tightly inserted into the neck of the tank and that the wick, the coating and stopper form an inseparable unit.

In particular, in the extreme lower part, the wick coating extends downwards forming two teeth, as a protection for the portion of wick protruding from the coating.

These two teeth face each other and may be connected at their respective ends, in order to form a lower stop for the wick.

This apparatus is therefore particularly suitable for places in which it is necessary to adopt adequate protection against domestic insects for long periods, and consequently has a longer operating period than that of the devices usually available on the market and which furthermore can be reused many times, requiring only the user to insert or remove the electrical connecting plug fitted at the end of the conductor of the apparatus or on the apparatus itself, or operate the relative switch.

BRIEF DESCRIPTION OF THE DRAWINGS

The invention will now be described on the basis of schematic drawings and exemplary embodiments, in which:

FIG. 1 shows a vertical longitudinal section of an apparatus directly provided with an electrical power plug;

FIG. 2 shows a plan view from above of the apparatus with the door, opposite the plug, open;

FIG. 3 is a front view of the apparatus, seen in the direction of the arrow F in FIG. 1;

DETAILED DESCRIPTION OF THE PREFERRED EMBODIMENTS

Figure 11:
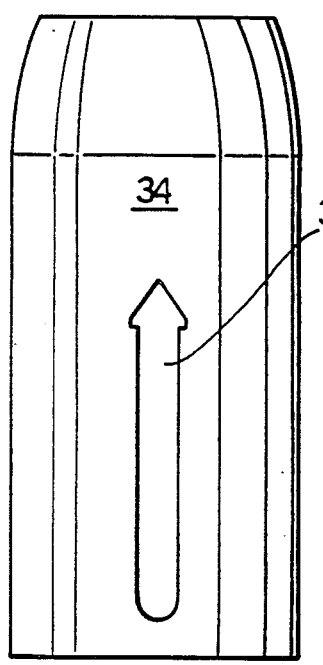
FIG. 11 shows the apparatus seen in the direction of the arrow F'.
Figure 9:
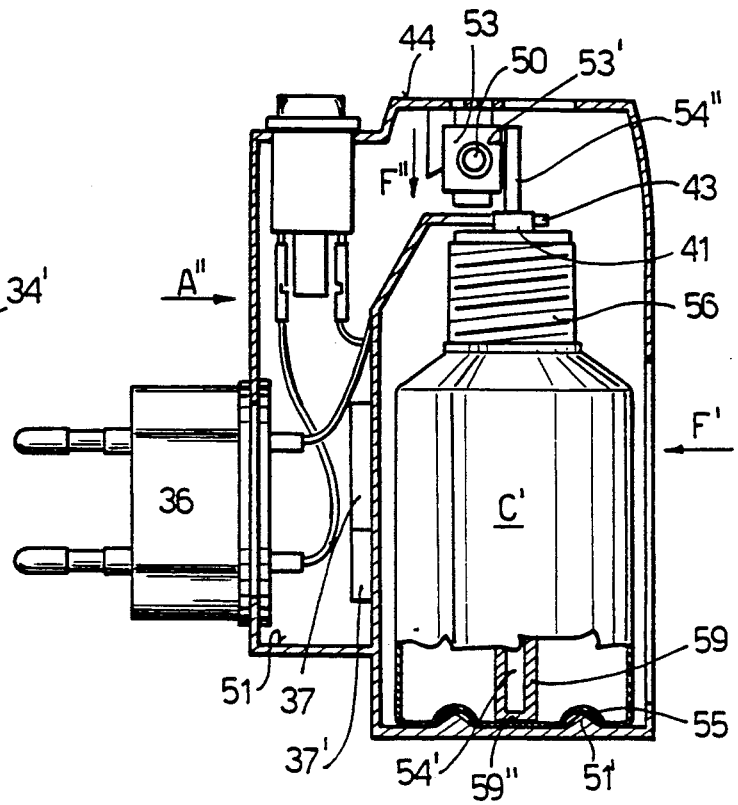
FIG. 9 is a longitudinal section of another example of the apparatus.

With reference to FIGS. 1 to 3, the apparatus comprises a box A made of artificial material. It consists essentially of two assemblies, the first of which, the lower assembly A', has a base 1, two sides 2, 2' and a front wall 3, set at right angles to each other. The wall 4, on the side facing away from the front wall 3, is shaped to form a semi-circle and advantageously serves as a door. The wall 4, when it serves as a door, is obtained in a single piece with one of the two sides 2' and is articulated on a vertical edge 2" of this side. The second assembly or cover 5 of the box is shaped on the outside like a parallelepiped, but with the front wall 3 prolonged downwards to partially house a rotating plug 6.

Said assemblies A' and 5 make up a single unit owing to the existence of means 7, 7' which can be spring engaged with one another.

The plug 6 rotably mounted on the front wall 3 of the box can turn through an angle of 90°.

Inside box A the wires 8 of the plug 6 are connected to a switch 9, preferably luminous, which protrudes a little from the top surface of the cover 5, to a possible timer and to a heating element 10. The latter element 10 is preferably in the form of a casehardened wire-wound resistance, in turn inserted into an axial through-hole 12 in a block 13, made of ceramic or appropriate artificial electrically insulating material, shaped like a parallelepiped and having a rectangular cross-section.

Instead of the plut 6 rotating 90°, the apparatus can be provided with a lead of a suitable length coming out of the box A, so that the apparatus can be placed at a distance from the power point.

The wick 14, more fully described later and of which only the extreme lower portion is in direct contact with the liquid, can be made of a cellulose or cotton linter based material, or of cotton linters along, formed of fibers from 3 to 6 mm long, consisting of almost pure cellulose, a material similar to that used for known mosquito repellent tablets. The material making up the wick 14 contains from 10% to 30%, preferably 20%, mineral dust, in particular basalt.

The heating element 10 advantageously consist of a thermistor which in turn is also protected by a covering.

Another solution can be offered by a resistance heating element, also protected by a covering.

The block 13, as described, which coaxially encloses the heating element 10, is housed in the extreme upper area of the box A or respectively of the cover 5, in which area a flat vertical wall 13' belonging to block 13 itself runs parallel to a portion of the flat vertical wall 5' of the cover 5.

On the outside of the cover 5 and when the apparatus is ready for use, the upper free portion 14" of the wick 14 is arranged with its wide flat wall, i.e. the widest wall, parallel and at a short distance d from the outer face of the above mentioned wall 5' of the cover 5. Preferably, according to the width of the wick 14, a cut not better illustrated is made to allow the wick 14 to reach within a short distance the above mentioned flat wall 13' of the block 13.

By maintaining a distance d, albeit short, between the corresponding longest flat wall 14''' of the wick 14 and the flat wall 13' of the block 13, the wick 14 or piece of cardboard is prevented from being damaged as a result of excessive heating, and constant, uniform evaporation of liquid over the whole free portion 14" of the wick 14 is ensured.

An annular portion 1' which emerges from the inside face of the base 1 of the apparatus in the box A supports a reservoir or container C, preferably made of pliable, transparent, artificial material. When new and unused, the container C is full of a liquid composed of substances which will be better specified below. The container C, which forms an integral part of the apparatus, can also be obtained separately, as a recharge.

The annular recess 15 on the bottom of the container C fits the raised annular portion 1' already described, which emerges from the base 1 of the box A, firmly setting the container C concentric to the raised portion 1'. The extreme lower portion 14' of the wick 14 then reaches into the concave area defined by the aforementioned annular recess 15. This concave area serves to ensure that the wick 14 is immersed during the final period of operation of the apparatus, avoiding wastage of even a small amount of liquid which, if it were distributed over the entire bottom surface and not collected therein, would wet the piece of cardboard only up to a much lower height than that required.

A screw cap 17 (FIG. 4), mounted externally on the neck 16 of the container C ensures that the container C and also the wick 14 are perfectly sealed, when the container is not in use.

Once again when the container C is not in use, provision is made for the cap 18 (FIG. 4) made of pliable material to be removably fitted onto the neck 16, to prevent the liquid contained in the container C from evaporating and thus condensing on the inner skirt of the external screw cap 17.

As can be clearly seen in FIG. 1, the free portion 14" of the wick 14 which protrudes upwards for a length s from a closing stopper 20 which will be better described later, is disposed with its smooth, flat, widest wall 14''' parallel and at a short distance d from the portion of wall 5' of the cover 5 or, when said flat wall 5' of the cover 5 has a cut (detail now shown in the drawing), parallel and at a short distance from the flat vertical wall 13' of the block 13.

Figure 5:
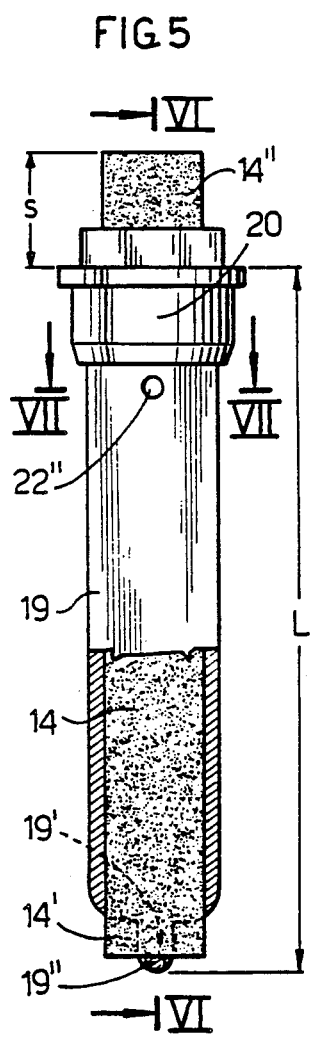
FIG. 5 is a partially cut-away view of a wick unit.

The wick 14, which is made in the form of a piece of thin cardboard, is enclosed for a length L (FIG. 5) in an impermeable coating or sheath 19. As a result of this, the liquid in the container C is absorbed solely by a short extreme lower portion 14 of the wick 14, not covered by the coating or sheath 19. The liquid rises in the wick 14 solely by capillarity, since there is no play between the outer surface of the wick 14 and the coating or sheath 19 and thus no possibility or infiltration of liquid along the section L.

More particularly, the chemical solution travels up the wick 14 by capillarity, starting from an area of the wick 14 near the base 1 of the container C where there is a lower temperature, to reach an area adjacent to a heat source 10 at a distance from said base 1 and on the outside of said container C, where there is a higher temperature.

Figure 4:
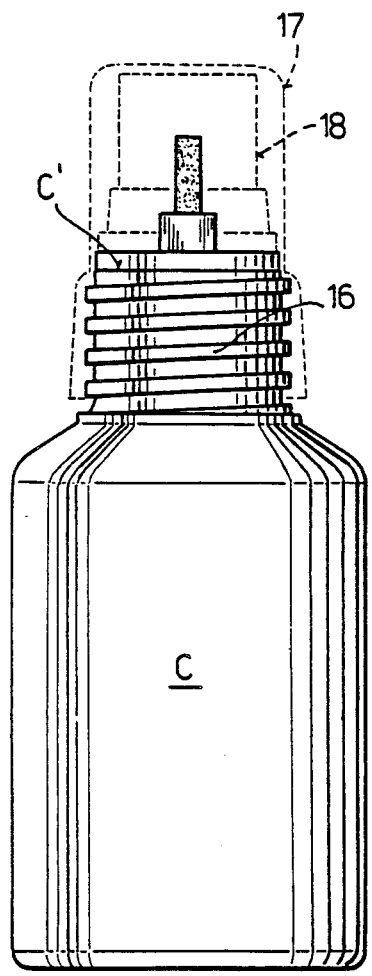
FIG. 4 shows a view of the container complete with stopper, sheath and wick.

In said upper area, the coating or sheath 19 of the wick 14 is surrounded by a closing device, in the form of the externally cylindrical stopper 20, which is tightly inserted into the neck 16 of the container C (FIG. 4).

The lower part of the coating or sheath 19 extends downwards in two teeth narrowed projections 19' of the same length as the lower free portion 14 of wick 14, said projections ensuring that the portion of thin cardboard that protrudes therefrom is mechanically protected during movement and automated insertion into the container C of the wick unit formed by the wick 14 itself, the coating or sheath 19 and the stopper 20. The two projections 19' can conveniently be joined at their ends by a small bridge 19" which creates a lower stop for the wick 14.

Figure 6:
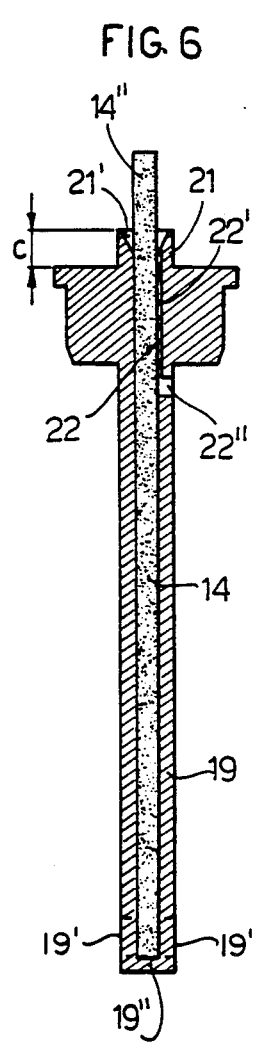
FIG. 6 is a section along the vertical plane VI—VI of FIG. 5.
Figure 7:
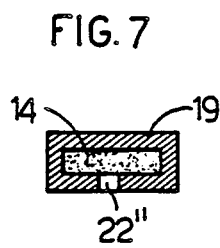
FIG. 7 is a section along the horizontal plane VII—VII of FIG. 5.
Figure 8:
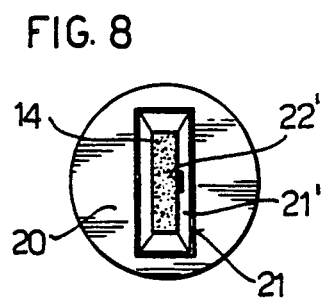
FIG. 8 is a view from above the wick unit in FIG. 5.

As shown in FIG. 6, a small continuous wall 21 extends from the upper wall of the stopper 20, surrounding the perimeter of the base of the protruding free portion 14" of the wick 14, creating a cup 21' to collect the liquid that condenses in order to prevent it from escaping.

In the upper part of the coating or sheath 19 a vent 22 is provided that allows air to pass from the outside to the inside of the container C, to compensate for possible pressure changes that would produce undesired effects. The hole 22 comprises a vertical upper section 22' which opens into the cup 21' and a lower horizontal section 22" which passes through the coating or sheath 19.

By creating the wick unit (FIG. 5) in the form of a wick 14, a coating or sheath 19 which encloses the wick 14 and a stopper 20, externally cylindrical thereof, it is possible to use a wick 14, preferably made of thin cardboard, which is an excellent absorbent medium. Lastly, this unit affords maximum safety for the user, since the wick 14 adheres closely to the sheat 19, making it impossible for liquid to escape from the container C, even if it is turned upside down.

Figure 12:
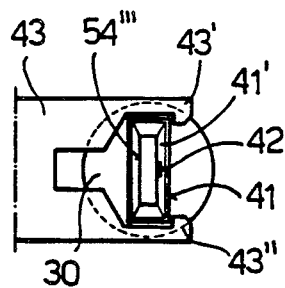
FIG. 12 represents a method of engaging the container housed in the box of the apparatus, seen from above.
Figure 10:
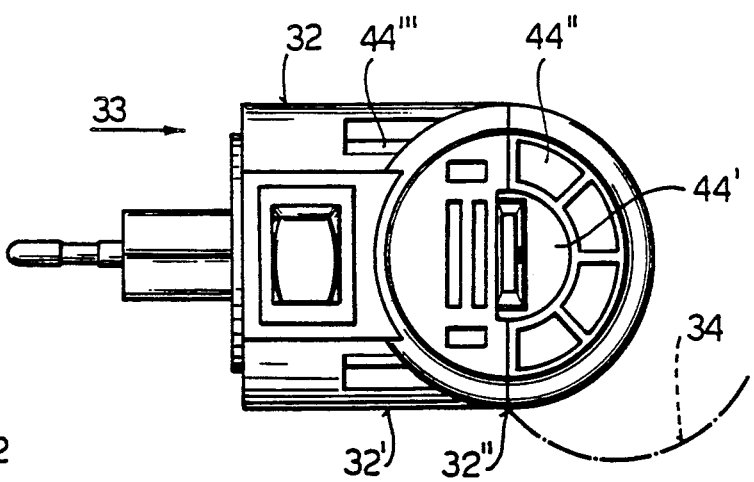
FIG. 10 is a plan view from above FIG. 9.

The apparatus as shown in FIGS. 9–12 is of a similar design to that of FIG. 1–8 and its various parts have been indicated increasing by at least ten the reference numbers used in FIGS. 1–8. It comprises a box A" which is composed essentially of two assemblies, connected in a preferably permanent manner by means of couplings 37, 37'. However, in this apparatus the extreme upper portion 54 of the wick 54 is completely enclosed inside the box A", the covering wall 44 of which is also provided with a plurality of opening 44', 44", 44''' to aid evaporation of the liquid and ensure cooling of the container C' in particular. Preferably, provision is made for the container C to be inserted through a door 34 provided with a longitudinal opening 34' to check the level of the liquid, and let in cooling air, this door 34 being obtained in a single piece with the box A". The container C' is fixed at the base in the same manner as that foreseen in FIG. 1, while at the top, in the portion of the stopper 30 (FIG. 12), the container C can optionally be spring engaged with the box A. To this end, provision is made for a pincer-shaped connection 43 to be used, provided with two sides claws 43', 43" each having teeth at the opposite ends, such as to engage elastically with the perimetral raised part 41 provided on the stopper 30 (FIG. 12). The connection 43 is obtained in a single piece with the box A".

A particular embodiment (not shown) provides for the apparatus to be made without a door. In this case, the container is positioned in its housing, providing for this purpose pliable connections on the shell of the container itself or even a cylindrical shaped raised part at the base of the box, so that the container can be inserted into it from above.

The wick 14, in the form of thin cardboard or similar pre-cut material, can be inserted into the preformed coating or sheath 19, or made at the same time as the latter. In this case a mould is forseen consisting of two half-moulds into which the pre-cut thin cardboard is inserted during the opening phase; these half-moulds are subsequently closed together and the plastic material is introduced into the free spaces, thus obtaining in a single operation the entire impermeable coating or sheath 19 around the wick 14.

The chemical solution held in the container, to which 0.5% to 1% anti-oxidant is added, consists of an active ingredient suitable for repelling domestic insects, chosen from the group of synthetic pyrethroids listed: bioallethrin, allethrin, etok, esbiothrin, cypermethrin, alphamethrin, vaporthrin, sumithrin, permethrin, or pyrethrum extract, alone or in combination, in a percentage of 2% to 8% in weight, particularly 3% to 5% in weight of esbiothrin, dissolved in a solvent chosen among the dearomatized aliphatic saturated hydrocarbons, having from 12 to 15 carbon atoms, alone or in combination, in a percentage from 98% to 92%, in particular 97% to 95% of tetradelane, known as C14.

Special attention has been devoted to the choice of solvents, which has extremely favorable toxicological characteristics, being a very pure product devoid of aromatic nuclei.

From what has been described the advantages of the apparatus in according with the invention compared with those of the prior art are clear. Thus, for example, the structure of the apparatus and particularly of the heating element and the wick, make it possible to insert the container C from the front, avoiding the difficulties of insertion from below, which could cause damage to the wick.

We claim:

1. An apparatus to keep flying insects away from people, comprising a box (1), a container (C, C') within the box, said container containing an evaporable liquid chemical product which, when evaporated, keeps flying insects away from people, a wick (14, 54) within the container, an impermeable sheath (19, 59) which covers the wick for almost the entire length of the wick but leaves free an extreme lower portion (14', 54') of the wick and an extreme upper portion (14", 54") of the wick which extreme upper portion protrudes from the container (C, C'), a heat source (10, 50) within the box, the heat source having a flat wall (13', 53') disposed at right angles to a base of said container, said extreme upper portion (14", 54") of said wick being disposed adjacent said flat wall (13', 53') of said heat source (10, 50).

2. An apparatus according to claim 1, characterized in that the wick (14, 54) has a rectangular cross section.

3. An apparatus according to claim 1, characterized in that a coating-free surface of the extreme lower portion (14', 54') is very small compared with that of the entire length of the wick (14, 15), while a coating-free surface of the extreme upper portion (14", 54") is larger than the surface of the lower portion and has an elongated shape.

4. An apparatus according to claim 1, characterized in that the liquid chemical product held in the container (C, C') advances by capillarity starting from an area of the wick (14, 54) near the base of the container (C, C'), where temperature is lower, until it reaches an area adjacent to the heat source (10, 50) at a distance from said base and outside said container (C, C'), where the temperature is higher.

5. An apparatus according to claim 1, characterized in that the wick (14, 54) consists of an absorbent material, in particular cardboard or a cellulose and/or cotton linter based material, containing from 10% to 30% and preferably 20% mineral dust, particularly basalt.

6. An apparatus according to claim 1, characterized in that the box (A, A") further comprises a means for closing the container (C, C'), in the form of an externally cylindrical stopper (20, 30) tightly inserted into a neck (16, 56) of the container (C, C') and in that the wick (14, 54), the sheath (19, 59) and the stopper (20, 30) form an inseparable unit.

7. An apparatus according to claim 6, characterized in that above the stopper (20, 30) a raised part (21, 41) is provided that surrounds a base of the extreme upper portion (14", 54") of the wick (14, 54) and creates a cup (21', 41') to collect condensed liquid.

8. An apparatus according to claim 7, characterized in that, in an upper part of the sheath (19, 59), a vent (22, 42) is provided to allow air to pass from outside to inside the container (C, C').

9. An apparatus according to claim 1, characterized in that, in its extreme lower part, the sheath (19, 59) of the wick (14, 54) extends in two narrowed projections (19', 59'), connected by a small bridge (19", 59"), to protect the extreme lower portion (14', 54') of the wick (14, 54) that protrudes from the sheath (19, 59).

10. An apparatus according to claim 1, characterized in that the box (A, A") comprises two assemblies that form a single unit, one of which has a wall that serves as a door (4, 34) which is articulated along a vertical edge (2", 32") of a side (2', 32') of the same assembly.

11. An apparatus according to claim 1, characterized in that an electrical power plug (6, 36), capable of rotating through an angle of 90°, is mounted on a front wall (3, 33) of the box (A, A") and has wires connected to a switch, preferably luminous, and to the heat source (10, 50).

12. An apparatus according to claim 4, characterized in that the heat source (10, 50) is a casehardened wire-wound resistance, inserted inside an axial through-hole in a block (13, 53) having one longitudinal flat wall (13', 53') set at 90° to the base of the container (C, C') and running parallel to the length of the wick (14, 54).

13. An apparatus according to claim 1, characterized in that the container (C, C') is made of pliable material and is supported by the base from which an annular rim (1', 51') protrudes, in order to create a complementary recess (15, 55) on a bottom of the container (C, C') into which the extreme lower portion (14', 54') of the wick (14, 54) reaches.

14. An apparatus according to claim 1, characterized in that the liquid chemical product placed in the container (C, C') is composed of an active ingredient, such as will repel domestic insects, chosen from the group of synthetic pyrethroids listed: bioallethrin, allethrin, etok, esbiothrin, cypermethrin, alphamethrin, vaporthrin, sumithrin, permethrin, and pyrethrum extract, alone or in combination, in a percentage of 2% to 8% in total weight, particularly 3% to 5% in weight of esbiothrin, dissolved in a solvent chosen among the dearomatized aliphatic saturated hydrocarbons, having from 12 to 15 carbon atoms, alone or in combination, in a percentage from 98% to 92%, particularly 97% to 95% of tetradecane, with the addition of 0.5% to 1% of anti-oxidant.

* * * * *